US010564170B2

(12) United States Patent
Schneider et al.

(10) Patent No.: US 10,564,170 B2
(45) Date of Patent: Feb. 18, 2020

(54) SAMPLE CONTAINER CARRIER, LABORATORY SAMPLE DISTRIBUTION SYSTEM AND LABORATORY AUTOMATION SYSTEM

(71) Applicant: Roche Diagnostics Operations, Inc., Indianapolis, IN (US)

(72) Inventors: Hans Schneider, Schwaikheim (DE); Christian Riether, Muehltal (DE); Michal Malinowski, Bietigheim-Bissingen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 120 days.

(21) Appl. No.: 15/860,750

(22) Filed: Jan. 3, 2018

(65) Prior Publication Data
US 2018/0128848 A1    May 10, 2018

Related U.S. Application Data

(63) Continuation of application No. PCT/EP2016/067135, filed on Jul. 19, 2016.

(30) Foreign Application Priority Data

Jul. 22, 2015    (EP) .................................... 15177890

(51) Int. Cl.
*B65G 54/02*        (2006.01)
*G01N 35/04*        (2006.01)

(52) U.S. Cl.
CPC ............. *G01N 35/04* (2013.01); *B65G 54/02* (2013.01); *G01N 2035/0477* (2013.01); *G01N 2035/0489* (2013.01)

(58) Field of Classification Search
CPC .......... G01N 35/04; G01N 2035/0489; G01N 2035/0477; B65G 54/02
USPC .................... 73/64.56, 863, 863.01, 863.91, 73/864.21–864.25, 864.31, 864.81, 73/864.91; 422/63–65, 67, 501, 547, 422/560–562
See application file for complete search history.

(56) References Cited

U.S. PATENT DOCUMENTS 3,273,727 A    9/1966    Rogers et al.
3,653,485 A    4/1972    Donlon
(Continued)

FOREIGN PATENT DOCUMENTS

CN    201045617 Y    4/2008
CN    102109530 A    6/2011
(Continued)

OTHER PUBLICATIONS

International Search Report dated Oct. 17, 2016, in Application No. PCT/EP2016/067135, 4 pp.

*Primary Examiner* — Robert R Raevis
(74) *Attorney, Agent, or Firm* — Roche Diagnostics Operations, Inc.

(57) ABSTRACT

A sample container carrier for a laboratory sample distribution system is presented. The sample container carrier comprises a magnetic element that is arranged such that a magnetic move force applied to the sample container carrier depends on an angularity. A laboratory sample distribution system comprising such a sample container carrier and a laboratory automation system comprising such a sample distribution system are also presented.

17 Claims, 4 Drawing Sheets

(56) References Cited

U.S. PATENT DOCUMENTS

| | | | |
|---|---|---|---|
| 3,901,656 A | 8/1975 | Durkos et al. | |
| 4,150,666 A | 4/1979 | Brush | |
| 4,395,164 A | 7/1983 | Beltrop et al. | |
| 4,544,068 A | 10/1985 | Cohen | |
| 4,771,237 A | 9/1988 | Daley | |
| 5,120,506 A | 6/1992 | Saito et al. | |
| 5,295,570 A | 3/1994 | Grecksch et al. | |
| 5,309,049 A | 5/1994 | Kawada et al. | |
| 5,350,564 A * | 9/1994 | Mazza | B01L 3/50855 422/562 |
| 5,457,368 A | 10/1995 | Jacobsen et al. | |
| 5,523,131 A | 6/1996 | Isaacs et al. | |
| 5,530,345 A | 6/1996 | Murari et al. | |
| 5,636,548 A | 6/1997 | Dunn et al. | |
| 5,641,054 A | 6/1997 | Mori et al. | |
| 5,651,941 A | 7/1997 | Stark et al. | |
| 5,720,377 A * | 2/1998 | Lapeus | B01L 9/06 198/346.1 |
| 5,735,387 A | 4/1998 | Polaniec et al. | |
| 5,788,929 A | 8/1998 | Nesti | |
| 6,045,319 A | 4/2000 | Uchida et al. | |
| 6,062,398 A | 5/2000 | Thalmayr | |
| 6,141,602 A | 10/2000 | Igarashi et al. | |
| 6,151,535 A | 11/2000 | Ehlers | |
| 6,184,596 B1 | 2/2001 | Ohzeki | |
| 6,191,507 B1 | 2/2001 | Peltier et al. | |
| 6,206,176 B1 | 3/2001 | Blonigan et al. | |
| 6,255,614 B1 | 7/2001 | Yamakawa et al. | |
| 6,260,360 B1 | 7/2001 | Wheeler | |
| 6,279,728 B1 | 8/2001 | Jung et al. | |
| 6,293,750 B1 | 9/2001 | Cohen et al. | |
| 6,429,016 B1 | 8/2002 | McNeil | |
| 6,444,171 B1 | 9/2002 | Sakazume et al. | |
| 6,571,934 B1 * | 6/2003 | Thompson | B65G 23/18 198/619 |
| 7,028,831 B2 | 4/2006 | Veiner | |
| 7,078,082 B2 | 7/2006 | Adams | |
| 7,122,158 B2 | 10/2006 | Itoh | |
| 7,278,532 B2 | 10/2007 | Martin | |
| 7,326,565 B2 | 2/2008 | Yokoi et al. | |
| 7,425,305 B2 | 9/2008 | Itoh | |
| 7,428,957 B2 | 9/2008 | Schaefer | |
| 7,578,383 B2 | 8/2009 | Itoh | |
| 7,597,187 B2 | 10/2009 | Bausenwein et al. | |
| 7,850,914 B2 | 12/2010 | Veiner et al. | |
| 7,858,033 B2 | 12/2010 | Itoh | |
| 7,875,254 B2 | 1/2011 | Garton et al. | |
| 7,939,484 B1 | 5/2011 | Loeffler et al. | |
| 8,240,460 B1 | 8/2012 | Bleau et al. | |
| 8,281,888 B2 | 10/2012 | Bergmann | |
| 8,502,422 B2 | 8/2013 | Lykkegaard | |
| 8,796,186 B2 | 8/2014 | Shirazi | |
| 8,833,544 B2 | 9/2014 | Stoeckle et al. | |
| 8,973,736 B2 | 3/2015 | Johns et al. | |
| 9,097,691 B2 | 8/2015 | Onizawa et al. | |
| 9,187,268 B2 | 11/2015 | Denninger et al. | |
| 9,211,543 B2 | 12/2015 | Ohga et al. | |
| 9,239,335 B2 | 1/2016 | Heise et al. | |
| 9,423,410 B2 | 8/2016 | Buehr | |
| 9,423,411 B2 | 8/2016 | Riether | |
| 9,567,167 B2 | 2/2017 | Sinz | |
| 9,575,086 B2 | 2/2017 | Heise et al. | |
| 9,593,970 B2 | 3/2017 | Sinz | |
| 9,598,243 B2 | 3/2017 | Denninger et al. | |
| 9,618,525 B2 | 4/2017 | Malinowski et al. | |
| 9,658,241 B2 | 5/2017 | Riether et al. | |
| 9,664,703 B2 | 5/2017 | Heise et al. | |
| 9,772,342 B2 | 9/2017 | Riether | |
| 9,791,468 B2 | 10/2017 | Riether et al. | |
| 9,810,706 B2 | 11/2017 | Riether et al. | |
| 10,126,317 B2 | 11/2018 | Heise et al. | |
| 10,197,586 B2 | 2/2019 | Sinz et al. | |
| 2002/0009391 A1 | 1/2002 | Marquiss et al. | |
| 2003/0092185 A1 | 5/2003 | Qureshi et al. | |
| 2004/0050836 A1 | 3/2004 | Nesbitt et al. | |
| 2004/0084531 A1 | 5/2004 | Itoh | |
| 2005/0061622 A1 | 3/2005 | Martin | |
| 2005/0109580 A1 | 5/2005 | Thompson | |
| 2005/0194333 A1 | 9/2005 | Veiner et al. | |
| 2005/0196320 A1 | 9/2005 | Veiner et al. | |
| 2005/0226770 A1 | 10/2005 | Allen et al. | |
| 2005/0242963 A1 | 11/2005 | Oldham et al. | |
| 2005/0247790 A1 | 11/2005 | Itoh | |
| 2005/0260101 A1 | 11/2005 | Nauck et al. | |
| 2005/0271555 A1 | 12/2005 | Itoh | |
| 2006/0000296 A1 | 1/2006 | Salter | |
| 2006/0047303 A1 | 3/2006 | Ortiz et al. | |
| 2006/0219524 A1 | 10/2006 | Kelly et al. | |
| 2007/0116611 A1 | 5/2007 | DeMarco | |
| 2007/0210090 A1 | 9/2007 | Sixt et al. | |
| 2007/0248496 A1 | 10/2007 | Bondioli et al. | |
| 2007/0276558 A1 | 11/2007 | Kim | |
| 2008/0012511 A1 | 1/2008 | Ono | |
| 2008/0029368 A1 | 2/2008 | Komori | |
| 2008/0056328 A1 | 3/2008 | Rund et al. | |
| 2008/0131961 A1 | 6/2008 | Crees et al. | |
| 2009/0004732 A1 | 1/2009 | LaBarre et al. | |
| 2009/0022625 A1 | 1/2009 | Lee et al. | |
| 2009/0081771 A1 | 3/2009 | Breidford et al. | |
| 2009/0128139 A1 | 5/2009 | Drenth et al. | |
| 2009/0142844 A1 | 6/2009 | Le Comte | |
| 2009/0180931 A1 | 7/2009 | Silbert et al. | |
| 2009/0322486 A1 | 12/2009 | Gerstel | |
| 2010/0000250 A1 | 1/2010 | Sixt | |
| 2010/0152895 A1 | 6/2010 | Dai | |
| 2010/0175943 A1 | 7/2010 | Bergmann | |
| 2010/0186618 A1 | 7/2010 | King et al. | |
| 2010/0255529 A1 | 10/2010 | Cocola et al. | |
| 2010/0300831 A1 | 12/2010 | Pedrazzini | |
| 2010/0312379 A1 | 12/2010 | Pedrazzini | |
| 2011/0050213 A1 | 3/2011 | Furukawa | |
| 2011/0124038 A1 | 5/2011 | Bishop et al. | |
| 2011/0172128 A1 | 7/2011 | Davies et al. | |
| 2011/0186406 A1 | 8/2011 | Kraus et al. | |
| 2011/0287447 A1 | 11/2011 | Norderhaug et al. | |
| 2012/0037696 A1 | 2/2012 | Lavi | |
| 2012/0129673 A1 | 5/2012 | Fukugaki et al. | |
| 2012/0178170 A1 | 7/2012 | Van Praet | |
| 2012/0211645 A1 | 8/2012 | Tullo et al. | |
| 2012/0275885 A1 | 11/2012 | Furrer et al. | |
| 2012/0282683 A1 | 11/2012 | Mototsu | |
| 2012/0286535 A1 | 11/2012 | Murakami | |
| 2012/0310401 A1 | 12/2012 | Shah | |
| 2013/0153677 A1 | 6/2013 | Leen et al. | |
| 2013/0180824 A1 | 7/2013 | Kleinikkink et al. | |
| 2013/0263622 A1 | 10/2013 | Mullen et al. | |
| 2013/0322992 A1 | 12/2013 | Pedrazzini | |
| 2014/0170023 A1 | 6/2014 | Saito et al. | |
| 2014/0234949 A1 | 8/2014 | Wasson et al. | |
| 2015/0014125 A1 | 1/2015 | Hecht | |
| 2015/0166265 A1 | 6/2015 | Pollack et al. | |
| 2015/0241457 A1 | 8/2015 | Miller | |
| 2015/0273468 A1 | 10/2015 | Croquette et al. | |
| 2015/0273691 A1 | 10/2015 | Pollack | |
| 2015/0276775 A1 | 10/2015 | Mellars et al. | |
| 2015/0276782 A1 | 10/2015 | Riether | |
| 2016/0003859 A1 | 1/2016 | Wenczel et al. | |
| 2016/0025756 A1 | 1/2016 | Pollack et al. | |
| 2016/0054341 A1 | 2/2016 | Edelmann | |
| 2016/0077120 A1 | 3/2016 | Riether | |
| 2016/0229565 A1 | 8/2016 | Margner | |
| 2016/0274137 A1 | 9/2016 | Baer | |
| 2016/0282378 A1 | 9/2016 | Malinowski et al. | |
| 2016/0341750 A1 | 11/2016 | Sinz et al. | |
| 2016/0341751 A1 | 11/2016 | Huber et al. | |
| 2017/0059599 A1 | 3/2017 | Riether | |
| 2017/0096307 A1 | 4/2017 | Mahmudimanesh et al. | |
| 2017/0097372 A1 | 4/2017 | Heise et al. | |
| 2017/0101277 A1 | 4/2017 | Malinowski | |
| 2017/0108522 A1 | 4/2017 | Baer | |
| 2017/0131307 A1 | 5/2017 | Pedain | |
| 2017/0131309 A1 | 5/2017 | Pedain | |
| 2017/0131310 A1 | 5/2017 | Volz et al. | |
| 2017/0138971 A1 | 5/2017 | Heise et al. | |

(56) References Cited

U.S. PATENT DOCUMENTS

| | | | |
|---|---|---|---|
| 2017/0160299 | A1 | 6/2017 | Schneider et al. |
| 2017/0168079 | A1 | 6/2017 | Sinz |
| 2017/0174448 | A1 | 6/2017 | Sinz |
| 2017/0184622 | A1 | 6/2017 | Sinz et al. |
| 2017/0248623 | A1 | 8/2017 | Kaeppeli et al. |
| 2017/0248624 | A1 | 8/2017 | Kaeppeli et al. |
| 2017/0363608 | A1 | 12/2017 | Sinz |
| 2018/0067141 | A1 | 3/2018 | Mahmudimanesh et al. |
| 2018/0106821 | A1 | 4/2018 | Vollenweider et al. |
| 2018/0156835 | A1 | 6/2018 | Hassan |
| 2018/0188280 | A1 | 7/2018 | Malinowski |
| 2018/0210000 | A1 | 7/2018 | van Mierlo |
| 2018/0210001 | A1 | 7/2018 | Reza |
| 2018/0217174 | A1 | 8/2018 | Malinowski |
| 2018/0224476 | A1 | 8/2018 | Birrer et al. |
| 2018/0348244 | A1 | 12/2018 | Ren |
| 2018/0348245 | A1 | 12/2018 | Schneider et al. |
| 2019/0018027 | A1 | 1/2019 | Hoehnel |
| 2019/0076845 | A1 | 3/2019 | Huber et al. |
| 2019/0076846 | A1 | 3/2019 | Durco et al. |
| 2019/0086433 | A1 | 3/2019 | Hermann et al. |
| 2019/0094251 | A1 | 3/2019 | Malinowski |
| 2019/0094252 | A1 | 3/2019 | Waser et al. |
| 2019/0101468 | A1 | 4/2019 | Haldar |

FOREIGN PATENT DOCUMENTS

| | | |
|---|---|---|
| DE | 3909786 A1 | 9/1990 |
| DE | 102012000665 A1 | 8/2012 |
| DE | 102011090044 A1 | 7/2013 |
| EP | 0601213 A1 | 10/1992 |
| EP | 0775650 A1 | 5/1997 |
| EP | 0916406 A2 | 5/1999 |
| EP | 1122194 A1 | 8/2001 |
| EP | 1524525 A1 | 4/2005 |
| EP | 2119643 A1 | 11/2009 |
| EP | 2148117 A1 | 1/2010 |
| EP | 2327646 A1 | 6/2011 |
| EP | 2447701 A2 | 5/2012 |
| EP | 2500871 A1 | 9/2012 |
| EP | 2502675 B1 | 2/2014 |
| EP | 2887071 A1 | 6/2015 |
| GB | 2165515 A | 4/1986 |
| JP | S56-147209 A | 11/1981 |
| JP | 60-223481 A | 11/1985 |
| JP | 61-081323 A | 4/1986 |
| JP | S61-069604 A | 4/1986 |
| JP | S61-094925 A | 5/1986 |
| JP | S61-174031 A | 8/1986 |
| JP | S61-217434 A | 9/1986 |
| JP | S62-100161 A | 5/1987 |
| JP | S63-31918 A | 2/1988 |
| JP | S63-48169 A | 2/1988 |
| JP | S63-82433 U | 5/1988 |
| JP | S63-290101 A | 11/1988 |
| JP | 1148966 A | 6/1989 |
| JP | H01-266860 A | 10/1989 |
| JP | H02-87903 A | 3/1990 |
| JP | 03-112393 A | 5/1991 |
| JP | 03-192013 A | 8/1991 |
| JP | H03-38704 Y2 | 8/1991 |
| JP | H04-127063 A | 4/1992 |
| JP | H05-69350 A | 3/1993 |
| JP | H05-142232 A | 6/1993 |
| JP | H05-180847 A | 7/1993 |
| JP | 06-26808 A | 2/1994 |
| JP | H06-148198 A | 5/1994 |
| JP | 06-156730 A | 6/1994 |
| JP | 06-211306 A | 8/1994 |
| JP | 07-228345 A | 8/1995 |
| JP | 07-236838 A | 9/1995 |
| JP | H07-301637 A | 11/1995 |
| JP | H09-17848 A | 1/1997 |
| JP | H11-083865 A | 3/1999 |
| JP | H11-264828 A | 9/1999 |
| JP | H11-304812 A | 11/1999 |
| JP | H11-326336 A | 11/1999 |
| JP | 2000-105243 A | 4/2000 |
| JP | 2000-105246 A | 4/2000 |
| JP | 2001-124786 A | 5/2001 |
| JP | 2001-240245 A | 9/2001 |
| JP | 2005-001055 A | 1/2005 |
| JP | 2005-249740 A | 9/2005 |
| JP | 2006-106008 A | 4/2006 |
| JP | 2007-309675 A | 11/2007 |
| JP | 2007-314262 A | 12/2007 |
| JP | 2007-322289 A | 12/2007 |
| JP | 2009-036643 A | 2/2009 |
| JP | 2009-062188 A | 3/2009 |
| JP | 2009-145188 A | 7/2009 |
| JP | 2009-300402 A | 12/2009 |
| JP | 2010-243310 A | 10/2010 |
| JP | 2010-271204 A | 12/2010 |
| JP | 2013-172009 A | 2/2013 |
| JP | 2013-190400 A | 9/2013 |
| SU | 685591 A1 | 9/1979 |
| WO | 1996/036437 A1 | 11/1996 |
| WO | 2003/042048 A3 | 5/2003 |
| WO | 2005/093433 A1 | 10/2005 |
| WO | 2007/024540 A1 | 3/2007 |
| WO | 2008/133708 A1 | 11/2008 |
| WO | 2009/002358 A1 | 12/2008 |
| WO | 2010/042722 A1 | 4/2010 |
| WO | 2012/170636 A1 | 7/2010 |
| WO | 2010/087303 A1 | 8/2010 |
| WO | 2010/129715 A1 | 11/2010 |
| WO | 2011/138448 A1 | 11/2011 |
| WO | 2012/142250 A1 | 10/2012 |
| WO | 2012/158541 A1 | 11/2012 |
| WO | 2013/152089 A1 | 10/2013 |
| WO | 2013/169778 A1 | 11/2013 |
| WO | 2013/177163 A1 | 11/2013 |
| WO | 2014/059134 A1 | 4/2014 |
| WO | 2014/071214 A1 | 5/2014 |
| WO | 2015/104263 A2 | 7/2015 |

* cited by examiner

SAMPLE CONTAINER CARRIER, LABORATORY SAMPLE DISTRIBUTION SYSTEM AND LABORATORY AUTOMATION SYSTEM

CROSS-REFERENCE TO RELATED APPLICATIONS

This application is a continuation of PCT/EP2016/067135, filed Jul. 19, 2016, which is based on and claims priority to EP 15177890.9, filed Jul. 22, 2015, which is hereby incorporated by reference.

BACKGROUND

The present disclosure relates to a sample container carrier for a laboratory sample distribution system, to a laboratory sample distribution system comprising such a sample container carrier, and to a laboratory automation system comprising such a laboratory sample distribution system.

Laboratory sample distribution systems comprising sample container carriers are typically used for laboratory automation systems. Such laboratory automation systems may comprise laboratory stations like pre-analytical, analytical and/or post-analytical stations.

An example for such a laboratory sample distribution system comprises a transport plane and a plurality of electro-magnetic actuators positioned below the transport plane. It further comprises a number of sample container carriers being adapted to carry sample containers. Such sample containers can, for example, be tubes made of transparent material.

However, there is a need for a sample container carrier having improved movement characteristics.

SUMMARY

According to the present disclosure, a sample container carrier for a laboratory sample distribution system is presented. The sample container carrier can be adapted to carry one or more sample containers. The sample container carrier can be adapted to be moved over a horizontal transport plane of the laboratory sample distribution system. The sample container carrier can comprise a magnetic element. The magnetic element can be adapted to interact with a magnetic field generated by the laboratory sample distribution system such that a magnetic move force is applied to the sample container carrier. The magnetic element can be arranged such that the magnetic move force can depend on an angularity of the sample container carrier placed on the transport plane.

In accordance with one embodiment of the present disclosure, a laboratory sample distribution system is presented. The laboratory sample distribution system can comprise a number of above sample container carriers, a transport plane adapted to support the sample container carriers, a number of electro-magnetic actuators stationary arranged below the transport plane, the electro-magnetic actuators adapted to generate a magnetic field to move the sample container carriers on top of the transport plane, and a control device configured to control the movement of the sample container carriers on top of the transport plane by driving the electro-magnetic actuators such that the sample container carriers move along corresponding transport paths.

Accordingly, it is a feature of the embodiments of the present disclosure to provide for a sample container carrier having improved movement characteristics. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
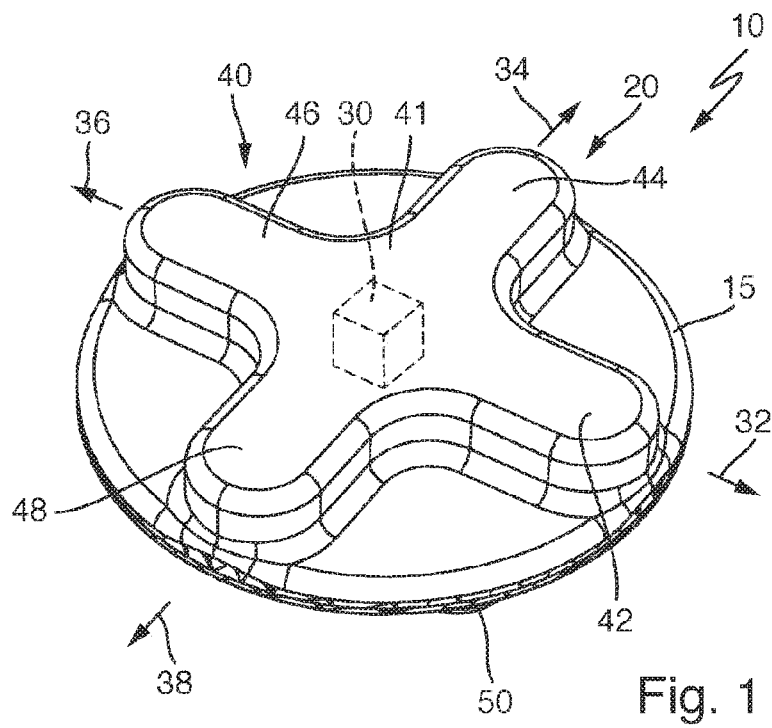
FIG. 1 illustrates a part of a sample container according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A sample container carrier for a laboratory sample distribution system is presented. The sample container carrier can be adapted to carry one or more sample containers, e.g. in form of conventional sample tubes.

The sample container carrier can be adapted to be moved over a horizontal transport plane of the laboratory sample distribution system. The sample container carrier can comprise a magnetic element. The magnetic element can be adapted to interact with a magnetic field generated by the laboratory sample distribution system such that a magnetic move force can be applied to the sample container carrier.

The magnetic element can be arranged such that the magnetic move force, for example amount and/or angle of the magnetic move force, can depend from an angularity of the sample container carrier being placed on, or moved over, the transport plane.

By use of a sample container carrier, it can be possible to introduce preferred directions in a sample container carrier. Compared to the prior art, which uses sample container carriers without preferred directions, effects like involuntary rotation of sample container carriers can be prevented. This can, for example, save energy and stabilize movement.

The term that the magnetic move force depends from an angularity may imply that the magnetic move force, for example the amount of the magnetic move force, can depend from an orientation of the sample container carrier relative to an external magnetic field. For example, if the sample container carrier is rotated by a certain amount around a vertical axis, the magnetic move force may have another amount or may point in another direction, although the sample container carrier is observed at the same position.

According to an embodiment, the magnetic element comprises a magnetically active device, especially in form of a permanent magnet. The magnetically active device can have a horizontal cross-section of a regular polygon. Preferably, it has a square cross-section.

By use of such a magnetic element, preferred directions can be introduced in a magnetic field generated by the magnetically active device. This can ascertain the dependence of the angularity of the magnetic move force, because the magnetic move force, in such a case, can typically depend on an angle between a respective preferred direction and an external magnetic field. For example, a preferred direction in which a magnetic field generated by the magnetically active device has a specifically high amount can be perpendicular to a side of the polygon.

According to an embodiment, the magnetic element can comprise a ferromagnetic, or ferromagnetic, guiding device. For example, the guiding device may be made of or comprise ferromagnetic or ferrimagnetic material.

The guiding device may be formed as a cover covering the magnetically active device at least partially, or completely. This can be used in order to easily implement preferred directions of a magnetic field generated by the magnetically active device using such a cover.

It can be understood that a guiding device in the sense as used here can be a guiding device for magnetic field lines. For example, such a guiding device can introduce preferred directions or can otherwise cause a deviation of the magnetic field generated by the magnetically active device from a state that would be present without such a guiding device.

According to an embodiment, the guiding device can have a horizontal cross-section comprising a number of sectors such as, for example, arms, wherein the sectors can be distant from each other and can be each originating at a common central part of the guiding device. These sectors can, for example, be used in order to guide the magnetic field generated by the magnetically active device. For example, each sector can correspond to a preferred direction. The sectors may be arranged to form a cross. This can, for example, be used in order to introduce four preferred directions having respective angles of about 90° between them.

The guiding device may be made of or comprise a material having a relative permeability $\mu_r$ larger than 1. In one embodiment, the relative permeability $\mu_r$ can be larger than 10. In another embodiment, the relative permeability $\mu_r$ can be larger than 100. In yet another embodiment, the relative permeability $\mu_r$ can be larger than 1,000. In still another embodiment, the relative permeability $\mu_r$ can be larger than 10,000.

The guiding device may be made of or comprise a magnetically soft material such as, for example construction steel. This material has been proven to show suitable properties for the intended use and is cheap and easily available.

According to an embodiment, the guiding device can comprise a plate positioned above the magnetically active device, wherein the plate can extend laterally beyond the magnetically active device.

According to an embodiment, laterally surrounding portions of the guiding device can be distant from the magnetically active device.

According to an embodiment, laterally surrounding portions of the guiding device and/or portions of the guiding device positioned above the magnetically active device can have a thickness adapted to prevent magnetic saturation at typical magnetic fields induced by the magnetically active device. Such typical magnetic fields can, for example, have a value of about 0.7 T. Saturation can lead to a decreased capability of the guiding device to bend or guide the magnetic field lines as intended.

Portions of the guiding device positioned above the magnetically active device may at least partially abut the magnetically active device. The guiding device may have the form of a cap imposed on the magnetically active device. The guiding device and the magnetically active device together may have the form of a mushroom. The magnetically active device can form the post. Such implementations have been proven useful for typical applications.

According to an embodiment, the sample container carrier can comprise a sliding member. The sliding member can be adapted to be in contact with the transport plane if the sample container carrier is placed on the transport plane. Such a sliding member can, for example, be used in order to adapt friction between the transport plane and the sample container carrier.

The sliding member may have a horizontal cross-section comprising a number of arms extending from a central part. The sliding member may have a concave horizontal cross-section between the arms. Such a configuration can especially increase stability of the sample container carrier when driving along an edge or a step in the transport plane.

The guiding device and the sliding member may define a cavity. The magnetically active device can be arranged inside the cavity. The guiding device may have an opening in the direction of the sliding member and the guiding device can at least partially laterally surround the magnetically active device. According to an implementation, it can surround the magnetically active device completely.

According to an embodiment, the sliding member can comprise a number of lower edges or borders, the lower edges surrounding a portion of the sliding member can be adapted to be in contact with the transport plane. The lower edges can be at least partially beveled. The beveling of the lower edges can increase from center to horizontal outer parts of the sliding member. Such an embodiment has especially been proven suitable for cases where the sample container carrier pass across a step in the transport plane.

According to an embodiment, the sliding member can have a centrally located recess not in contact with the transport plane. The recess can be surrounded by a portion of the sliding member adapted to be in contact with the transport plane. Such an embodiment has been proven useful to reduce friction between the sample container carrier and the transport plane and to stabilize the sample container carrier during movement.

A laboratory sample distribution system is also presented. The laboratory sample distribution system can comprise a number of sample container carriers. With regard to the sample container carriers, all discussed implementations, variations and embodiments can be used. The laboratory sample distribution system can further comprise a transport plane adapted to support the sample container carriers.

The laboratory sample distribution system can further comprise a number of electro-magnetic actuators stationary arranged below the transport plane. The electro-magnetic actuators can be adapted to generate a magnetic field to move the sample container carriers on top of the transport plane.

The laboratory sample distribution system can further comprise a control device configured to control the movement of the sample container carrier on top of the transport plane by driving the electro-magnetic actuators such that the sample container carriers move along corresponding transport paths.

For example, the laboratory sample distribution system can comprise a number of 1 to 500 sample container carriers. It can also comprise a number of 4 to 1024 electro-magnetic actuators. The transport plane can also be denoted as a transport surface. Supporting the sample container carriers can also be denoted as carrying the sample container carriers. The electro-magnetic actuators of the laboratory sample distribution system may be used in order to generate magnetic fields that drive the sample container carriers over the transport plane. The sample container carriers can be moved in two dimensions, allowing for great flexibility when transporting sample container carriers, for example between laboratory stations. The distance between electro-magnetic actuators in a typical implementation can be about 20 mm or about 20 mm.

According to an embodiment, the electro-magnetic actuators, especially respective magnetic coils, and/or magnetic cores, can have a horizontal cross-section of a regular polygon. In one embodiment, they can have a square cross-section. Such a configuration can be used in order to introduce preferred directions in the magnetic field generated by the electro-magnetic actuators. This can especially be used in order to further direct movement of the sample container carriers on the transport plane along certain orientations or directions.

The transport plane can be made of electroconductive material and can be grounded. The ferromagnetic, or ferromagnetic, guiding device may also be formed of electroconductive material, e.g. iron steel, etc. The guiding device may have a cap-shape or bell-shape. A lower end of the guiding device, defining an opening of the cap or bell, can be adapted to be in direct contact with the transport plane if the sample container carrier is placed on the transport plane. The guiding device and the transport plane can define a cavity if the sample container carrier is placed on the transport plane. The magnetic element can be arranged inside the cavity. The magnetic element can be fixed to the guiding device at an upper end of the guiding device. The guiding device can comprise a holder for a sample container, e.g. placed at an upper end of the guiding device. The holder may e.g. be embodied as a blind hole, e.g. having a circular cross section, adapted to receive the sample container. This embodiment can prevent an electrostatic charging of the transport plane and of the sample container carriers when the sample container carriers move over the transport plane.

A laboratory automation system comprising a number of pre-analytical, analytical and/or post-analytical (laboratory) stations and a laboratory sample distribution system as described above adapted to transport the sample container carriers and/or sample containers between the laboratory stations is also presented. The laboratory stations may be arranged adjacent to the laboratory sample distribution system.

Pre-analytical stations may be adapted to perform any kind of pre-processing of samples, sample containers and/or sample container carriers.

Analytical stations may be adapted to use a sample or part of the sample and a reagent to generate a measuring signal, the measuring signal indicating if and in which concentration, if any, an analyte exists.

Post-analytical stations may be adapted to perform any kind of post-processing of samples, sample containers and/or sample container carriers.

The pre-analytical, analytical and/or post-analytical stations may comprise at least one of a decapping station, a recapping station, an aliquot station, a centrifugation station, an archiving station, a pipetting station, a sorting station, a tube type identification station, and a sample quality determining station.

Referring initially to FIG. 1, FIG. 1 shows a part of a sample container carrier 10. In detail, FIG. 1 shows a bottom part of a sample container carrier 10, i.e. elements of the sample container carrier 10 arranged just below and above a bottom plate 15.

On the bottom plate 15, a magnetic element 20 can be arranged. The magnetic element 20 can comprise a magnetically active device in the form of a permanent magnet 30. The permanent magnet 30 can have a square horizontal cross-section.

The magnetic element 20 can further comprise a guiding device 40 that can be imposed over the permanent magnet 30. The guiding device 40 can comprise a first arm 42, a second arm 44, a third arm 46 and a fourth arm 48. The guiding device 40 can be made of a magnetically highly permeable material.

By the guiding device 40 having arms 42, 44, 46, 48 and a specific shape of the permanent magnet 30, the resulting magnetic field can be specifically tailored, such that four preferred directions can result, namely a first preferred direction 32 oriented along the first arm 42, a second preferred direction 34 oriented along the second arm 44, a third preferred direction 36 oriented along the third arm 46, and a fourth preferred direction 38 oriented along the fourth arm 48. These preferred directions can provide for the effect that a magnetic move force that can be applied to the sample container carrier 10 when an external magnetic field is present can depend from an angularity, i.e. an angular orientation of the sample container carrier 10.

As depicted in FIG. 1, the arms 42, 44, 46, 48 of the guiding device can be arranged to form a total of four sectors that can be arranged to form a cross. In other words, respective angles between the arms 42, 44, 46, 48 or between sectors defined by these arms 42, 44, 46, 48 can have a value of about 90° respectively. It can be noted that an angle between arms or sectors can be typically defined as an angle between respective distinguished directions of the arms or sectors, e.g. directions defining a center and/or symmetry axis.

The arms 42, 44, 46, 48 can respectively originate at a common central part 41 of the guiding device 40. This central part 41 can overlap the permanent magnet 30. By such a configuration, the guiding device 40 can have the form of a cap imposed on the permanent magnet 30.

On the other side of the bottom plate 15, a sliding member 50 can be arranged. This sliding member 50 is only visible in FIG. 1 with a very small part and will be further explained with reference to FIG. 2.

Figure 2:
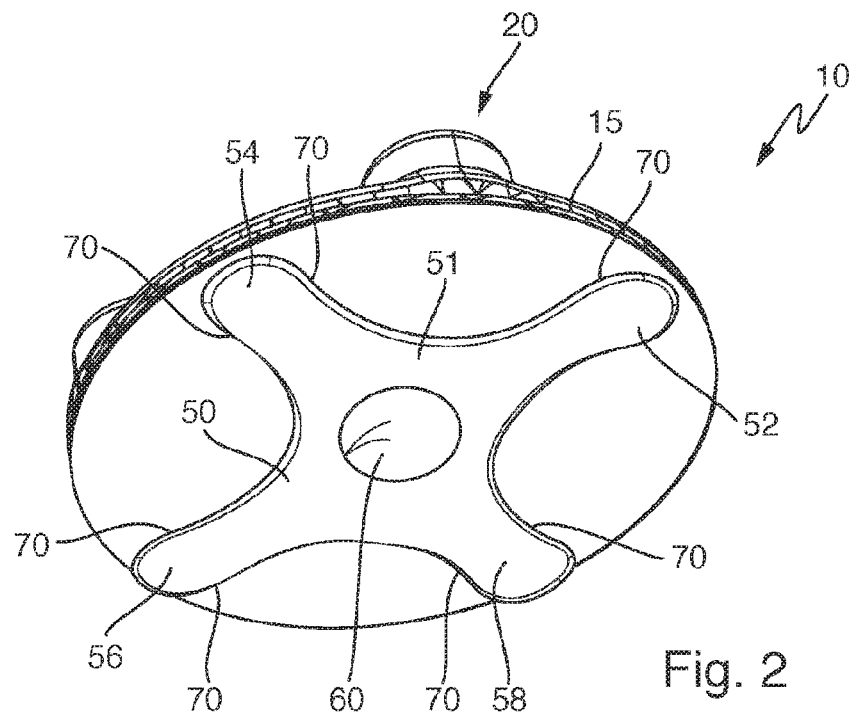
FIG. 2 illustrates the part of FIG. 1 in a different perspective according to an embodiment of the present disclosure.

FIG. 2 shows the part of the sample container carrier 10 of FIG. 1 from another perspective. In detail, a bottom side of the sample container carrier 10 is shown.

The sliding member 50 can comprise four arms 52, 54, 56, 58, which can be arranged with horizontal angles of about 90° in between such that they can form a cross. The arms 52, 54, 56, 58 can each have a cross-section that can be tapering from an inner part 51 to respective outer parts, wherein the outer parts can be round. This configuration can enhance the stability of the sample container carrier 10 especially in those cases when two of three arms 52, 54, 56, 58 are positioned on an upper side of a step formed in a transport plane on which the sample container carrier 10 is moving. In detail, it can be easily recognized that in such a case, two of the arms can be on an upper part and two of the arms can be on a lower part so that the sample container carrier 10 can move without any risk of tilting.

In order to ease climbing of the sample container carrier 10 on a step formed in the transport plane, respective lower edges 70 of the arms 52, 54, 56, 58 can be beveled, wherein the beveling can increase from the central part 51 to respective outer parts of the arms 52, 54, 56, 58. By such beveling, a step in the transport plane on which the sample container carrier 10 is moving can lead to a smooth lifting of the sample container carrier 10 so that it may not bounce against the step.

Centrally in the sliding member 50, a recess 60 can be located. The recess 60 can be surrounded by parts of the sliding member 50 that are in contact with a transport plane when the sample container carrier 10 is moving on the transport plane, but can reduce the total contact area between the sliding member 50 and the transport plane. Thus, friction can be reduced, which can have a positive effect on energy consumption.

Figure 3:
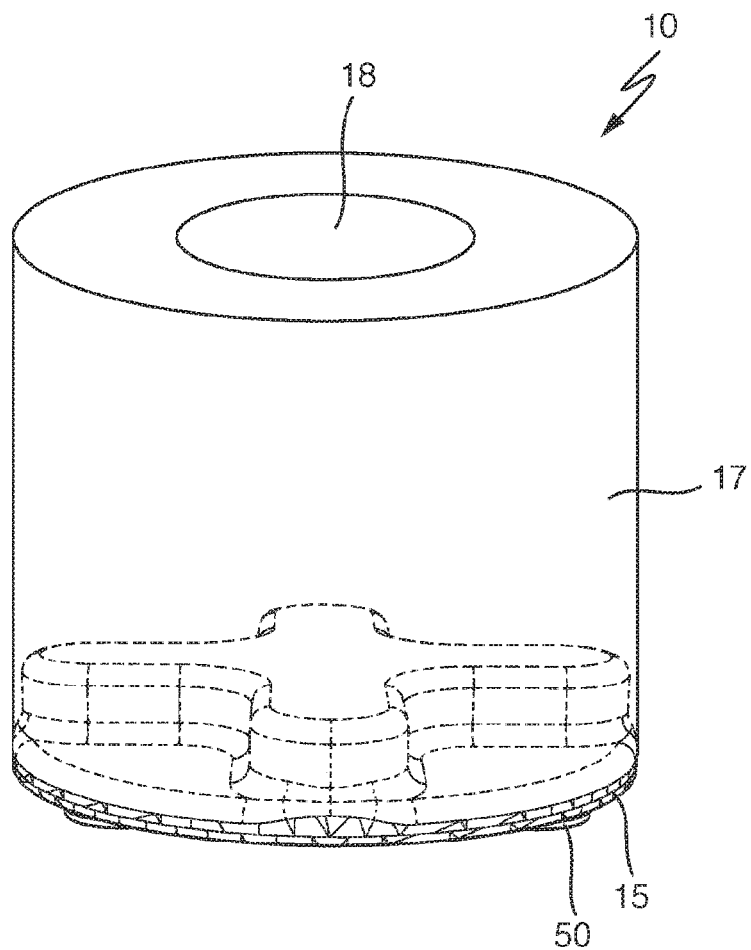
FIG. 3 illustrates a sample container comprising the part of FIGS. 1 and 2 according to an embodiment of the present disclosure.

FIG. 3 shows a complete sample container carrier 10 in a perspective view. The sample container carrier 10 can comprise the base plate 15 at its lower end with the sliding member 50 positioned below the base plate 15. This can allow the sample container carrier 10 to move on a transport plane of a sample distribution system.

The sample container carrier 10 can comprise a main body 17 that can be positioned above the base plate 15. In the main body 17, a sample container holder 18 can be arranged. The sample container holder 18 can be embodied as a hole in which a sample container can be placed and can be held.

Figure 4:
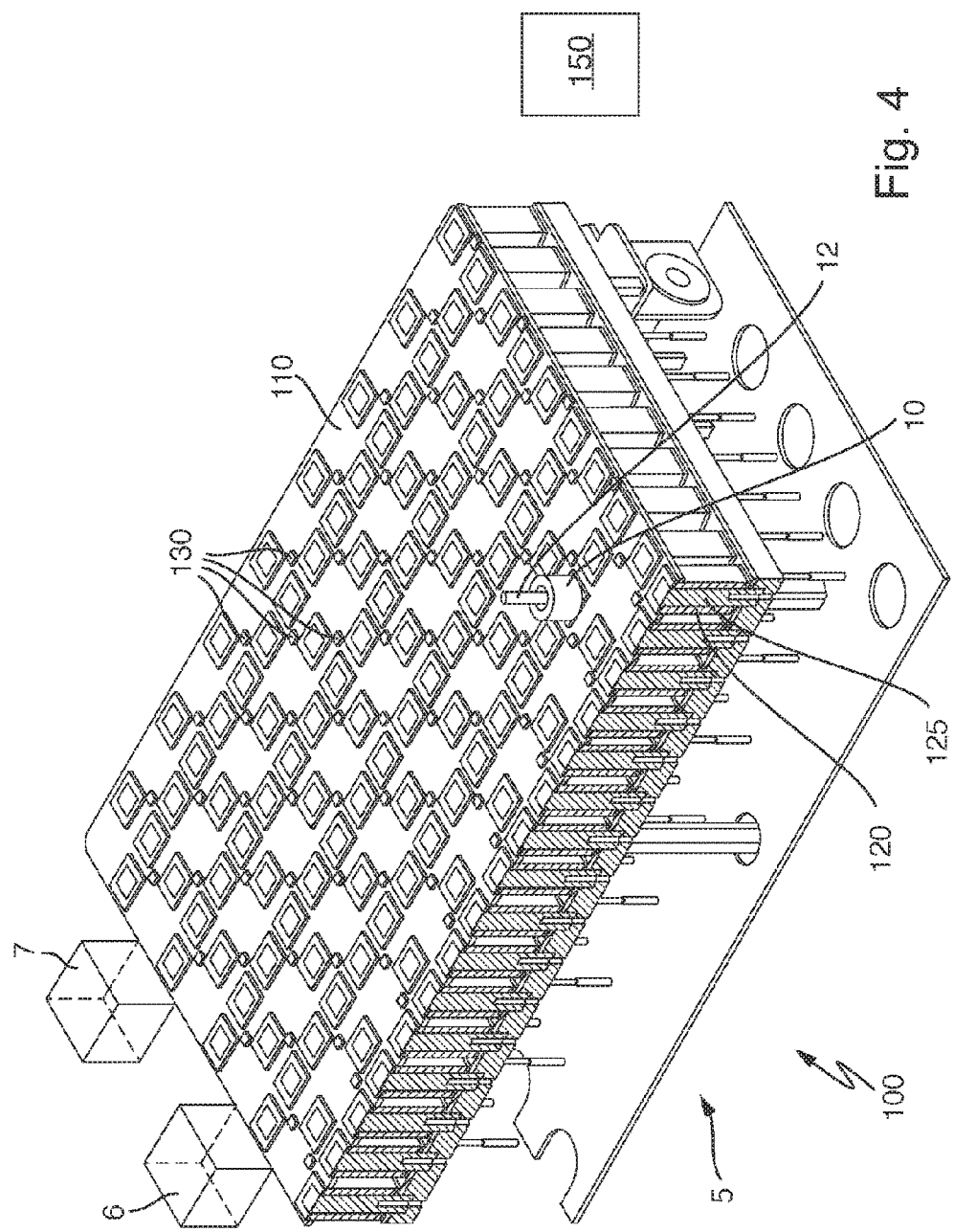
FIG. 4 illustrates a laboratory sample distribution system according to an embodiment of the present disclosure.

FIG. 4 shows a laboratory automation system 5 having a sample distribution system 100. The laboratory automation system 5 can comprise a first laboratory station 6 and a second laboratory station 7. These are shown for illustrative purposes only. It can be noted that typical laboratory automation systems 5 can comprise a plurality of laboratory stations that can be arranged besides the sample distribution system 100 such that the sample distribution system 100 can be used in order to transport samples or sample containers between the laboratory stations 6, 7.

The laboratory sample distribution system 100 can comprise a transport plane 110 on which sample container carriers 10 can move. For illustrative purposes only, a single sample container carrier 10 according to FIG. 3 is shown on the transport plane 110. The sample container carrier 10 can contain a sample container 12 that can be embodied as a conventional laboratory tube. It can be noted that on typical sample distributions systems 100, a plurality of sample container carriers carrying respective sample containers can be arranged.

The sample distribution system 100 can further comprise a number of electro-magnetic actuators 120 embodied as coils with respective magnetic cores 125. Both the electro-magnetic actuators 120 and the cores 125 can have a square cross shape in a horizontal plane. Thus, they can produce a magnetic field with respective preferred directions substantially perpendicular to edges of the square cross-section. This measure can help in guiding the sample container carrier 10 along a specific path.

On the transport plane 110, there can be arranged a plurality of position sensors 130 that can be adapted to sense a position of a sample container carrier 10 by sensing the magnetic field generated by the permanent magnet 30 of the respective sample container carrier 10. The sample distribution system 100 can further comprise an electronic control unit 150. The electronic control unit 150 can be adapted to control the electro-magnetic actuators 120 and to receive signals from the position sensors 130. Thus, the control unit 150 can actively move a sample container carrier 10 using the electro-magnetic actuators 120. It can also sense the position of the sample container carrier 10 using the position sensors 130. Using this functionality, the electronic control unit 150 can move a respective sample container carrier 10 along a predetermined transport path.

It can be noted that the electronic control unit 150 can generally comprise a processor and a memory, wherein the memory can comprise program code that can cause the processor, when executed, to perform in a certain way, for example to sense a position of a sample container carrier 10 and/or to move the sample container carrier 10 along a transport path.

By the laboratory sample distribution system 5, the task of transporting samples or sample containers between laboratory stations 6, 7 can be performed, wherein rotation of the sample container carrier 10 can be prevented due to the preferred directions of both the sample container carrier 10 and the electro-magnetic actuators 120 with their respective cores 125. This can save energy and lead to straighter transport paths that can improve system throughput.

Figure 5:
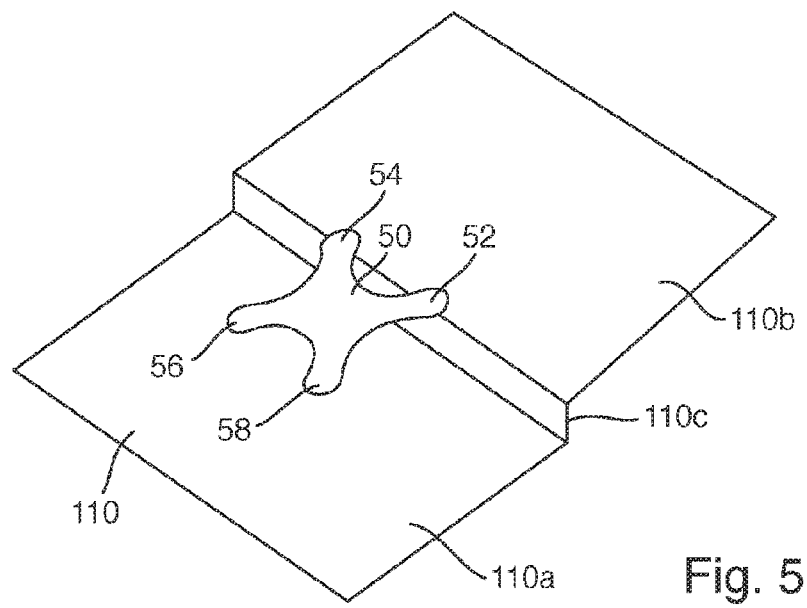
FIG. 5 illustrates a sliding member of a sample container at a step according to an embodiment of the present disclosure.

FIG. 5 shows the transport plane 110 in a case where the transport plane 110 can comprises a step 110c. On the left side of the step 110c, there can be a lower portion 110a of the transport plane 110. On the right side of the step 110c, there can be an upper part 110b of the transport plane 110. For illustrative purposes only, the transport plane 110 is shown in FIG. 5 without the electro-magnetic actuators 120, the magnetic cores 125 and the position sensors 130.

It can be noted that the step 110c as shown in FIG. 5 can, for example, arise at a line at which two modules of the sample distribution system 110 abut each other.

To illustrate the advantageous configuration of the sliding member 50, the sliding member 50 of FIG. 2 is shown separately and schematically without the remaining parts of the sample container carrier 10. As depicted, the first arm 52 and the second arm 54 can extend on the upper part 110b of the transport plane 110, whereas the third arm 56 and the fourth arm 58 can remain on the lower part 110a of the transport plane 110. However, the sliding member 50 can remain in contact with the transport plane 110 at four positions, thus preventing tilting or any other instability that could arise when round sliding members 50 are used.

Figure 6:
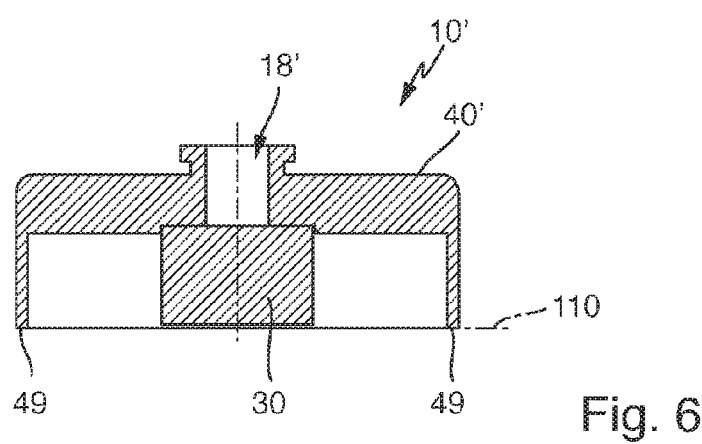
FIG. 6 illustrates a sample container according to another embodiment of the present disclosure.

FIG. 6 shows a sample container carrier 10' according to a further embodiment in a sectional view. The sample container carrier 10' can comprise the magnetically active device in the form of a permanent magnet 30 and a bell-shaped guiding device 40' formed of electroconductive material, e.g. iron steel. A lower portion 49 of the guiding device 40', defining an opening of the guiding device 40', can be adapted to be in direct contact with the transport plane 110 if the sample container carrier 10' is placed on the transport plane 110. The guiding device 40' and the transport plane 110 can define a cavity if the sample container carrier 10' is placed on the transport plane 110. The magnetically active device 30 can be arranged inside the cavity. The magnetically active device 30 can be fixed to the guiding device 40' at an upper end of the guiding device 40'. The guiding device 40' can comprise a holder 18' for a sample container. The holder 18' can be embodied as a blind hole in the guiding device 40' having a circular cross section, adapted to receive a sample container. The transport plane 110 according to this embodiment can be made of electroconductive material and can be grounded. This embodiment can prevent an electrostatic charging of the transport plane 110 and of the bottom 49 of the sample container carriers 10', if the sample container carriers 10' move over the transport plane 110.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A laboratory sample distribution system, the laboratory sample distribution system comprising:
   a number of sample container carriers, wherein the sample container carrier is configured to carry one or more sample containers, wherein the sample container carrier is configured to be moved over a horizontal transport plane of the laboratory sample distribution system, and wherein the sample container carrier comprises a magnetic element, wherein the magnetic element is configured to interact with a magnetic field generated by the laboratory sample distribution system such that a magnetic move force is applied to the sample container carrier and wherein the magnetic element is arranged such that the magnetic move force depends on an angularity of the sample container carrier placed on the transport plane;
   a transport plane configured to support the sample container carriers;
   a number of electro-magnetic actuators stationary arranged below the transport plane, the electro-magnetic actuators configured to generate a magnetic field to move the sample container carriers on top of the transport plane; and
   a control device configured to control the movement of the sample container carriers on top of the transport plane by driving the electro-magnetic actuators such that the sample container carriers move along corresponding transport paths.

2. The sample container carrier according to claim 1, wherein the magnetic element comprises a magnetically active device and wherein the magnetically active device has a horizontal cross section of a regular polygon.

3. The sample container carrier according to claim 2, wherein the magnetically active device is a permanent magnet.

4. The sample container carrier according to claim 2, wherein the regular polygon is a square.

5. The sample container carrier according to claim 2, wherein the magnetic element comprises a ferromagnetic or ferrimagnetic guiding device.

6. The sample container carrier according to claim 5, wherein the guiding device is formed as a cover covering the magnetically active device at least partially.

7. The sample container carrier according to claim 6, wherein the guiding device has a horizontal cross section comprising a number of sectors and wherein the sectors are distant from each other and are each originating at a common central part of the guiding device.

8. The sample container carrier according to claim 7, wherein the number of sectors are embodied as arms.

9. The sample container carrier according to claim 7, wherein the sectors are arranged to form a cross.

10. The sample container carrier according to claim 1, further comprises
    a sliding member, wherein the sliding member is configured to be in contact with the transport plane if the sample container carrier is placed on the transport plane.

11. The sample container carrier according to claim 10, wherein the sliding member has a horizontal cross section comprising a number of arms extending from a central part and wherein the sliding member has a concave horizontal cross section between the arms.

12. The sample container carrier according to claim 10, wherein the sliding member comprises a number of lower edges, the lower edges surrounding a portion of the sliding member configured to be in contact with the transport plane and wherein the lower edges are at least partially bevelled.

13. The sample container carrier according to one of claims 10, wherein the sliding member has a centrally located recess in which the sliding member is not in contact with the transport plane, the recess being surrounded by a portion of the sliding member configured to be in contact with the transport plane.

14. The laboratory sample distribution system according to claim 1, wherein the electro-magnetic actuators have a horizontal cross section of a regular polygon.

15. The laboratory sample distribution system according to claim 14, wherein the electro-magnetic actuators are respective magnetic coils.

16. A laboratory automation system, the laboratory automation system comprising:
    a number of laboratory stations; and
    a laboratory sample distribution system according to claim 1 adapted to distribute sample container carriers and/or sample containers between the laboratory stations.

17. The laboratory automation system according to claim 16, wherein the number of laboratory stations are in the form of pre-analytical stations, analytical stations and/or post-analytical stations.

* * * * *